(12) United States Patent
Awaad et al.

(10) Patent No.: US 9,598,361 B1
(45) Date of Patent: Mar. 21, 2017

(54) AMINO SUBSTITUTED ACETAMIDE DERIVATIVE

(71) Applicant: KING SAUD UNIVERSITY, Riyadh (SA)

(72) Inventors: Amani Shafeek Awaad, Riyadh (SA); Ahmed Mahmoud Ahmed Alafeefy, Riyadh (SA); Reham Mostafa El-Meligy, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/097,261

(22) Filed: Apr. 12, 2016

(51) Int. Cl.
C07C 311/46 (2006.01)
C07C 303/40 (2006.01)
C07D 211/62 (2006.01)
C07D 211/48 (2006.01)
C07D 211/18 (2006.01)
C07D 211/58 (2006.01)
C07D 211/22 (2006.01)
C07D 295/15 (2006.01)
C07D 215/42 (2006.01)

(52) U.S. Cl.
CPC .......... C07C 311/46 (2013.01); C07C 303/40 (2013.01); C07D 211/18 (2013.01); C07D 211/22 (2013.01); C07D 211/48 (2013.01); C07D 211/58 (2013.01); C07D 211/62 (2013.01); C07D 215/42 (2013.01); C07D 295/15 (2013.01)

(58) Field of Classification Search
CPC ... C07C 311/46; C07C 303/40; C07D 211/62; C07D 211/48; C07D 211/18; C07D 211/58; C07D 211/22; C07D 295/15; C07D 215/42
See application file for complete search history.

(56) References Cited

U.S. PATENT DOCUMENTS 5,192,774 A      3/1993   Shinozaki et al.
5,932,598 A *    8/1999   Talley .................... A61K 31/18
                                                              514/341
6,403,607 B1     6/2002   Hidaka et al.

* cited by examiner

Primary Examiner — Erich A Leeser
(74) Attorney, Agent, or Firm — Richard C. Litman

(57) ABSTRACT

An amino substituted acetamide derivative can include a compound having the following general formula:

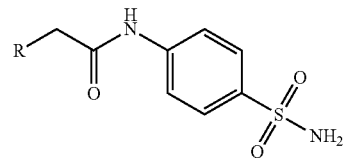

wherein R represents (4-Cyano-4-phenyl)piperidinyl hydrochloride, (4-Hydroxy-4-phenyl)piperidine, (4-chlorophenyl)piperidine hydrochloride, 4-Piperidinopiperidine, 4-(Methoxyphenyl)piperidine, 1-(2,3-xylyl)piperazine monohydrochloride, 4-Aminoquinaldine or anthranilic acid, or a pharmaceutically acceptable salt thereof.

4 Claims, 4 Drawing Sheets

AMINO SUBSTITUTED ACETAMIDE DERIVATIVE

BACKGROUND OF THE INVENTION

1. Field of the Invention

The present invention relates to anti-ulcer drugs, and particularly to anti-ulcerogenic and anti-ulcerative colitis (UC) amino substituted acetamide derivative.

2. Description of the Related Art

Ulcers in the gastrointestinal tract can be categorized as one of two common types according to location; ulcerative colitis (lower) and peptic ulcer (upper). Ulcerative colitis (UC) is an inflammatory bowel disease that primarily affects the colonic mucosa. In its most limited form, it may be restricted to the distal rectum, while in its most extended form, the entire colon is involved (Awaad et al, 2012). UC can occur in both sexes and in any age group but most often begins in people between 15 and 30 years of age. The exact causes of UC are still not clear but different factors have been postulated as possible etiologic agents, e.g., genetic factors, infective agents, immunological basis, smoking, medications and pathological factors.

Different heterocyclic compounds have been synthesized by a large number of research efforts and some derivatives have been found to possess antitumor, anti-diabetic, antimicrobial, anticonvulsant, anti-ulcer and anthelmintic activities. For example, the small and simple benzothiazole nucleus and its derivatives possess various diverse biological properties. Substituted fluorenyl derivatives such as the 9-fluorenyl amine derivatives has moderate biological activity on cancer. Many of these compounds, however, are associated with harmful side effects. Anti-ulcer compounds that are effective against ulcerative colits (UC) as well as peptic ulcers, with little or no side effects, are desirable.

Thus, amine substituted acetamide derivatives possessing antiulcerogenic and anti-ulcerative colitis activities solving the aforementioned problems is desired.

SUMMARY OF THE INVENTION

An amino substituted acetamide derivative can include a compound having the following general formula:

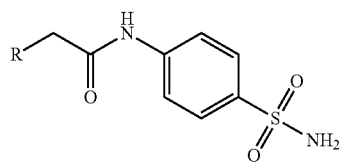

wherein R represents at least one of the following amino substituents,

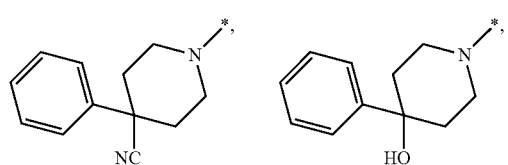

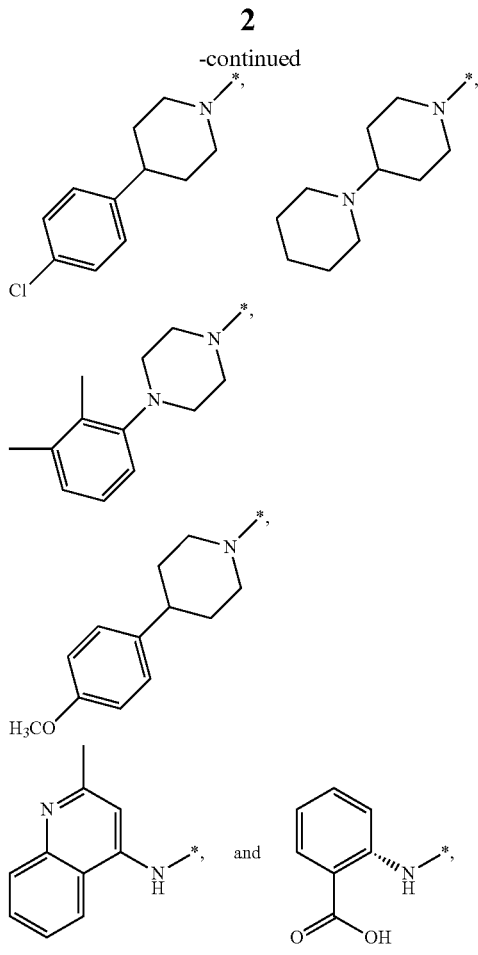

or a pharmaceutically acceptable salt thereof.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
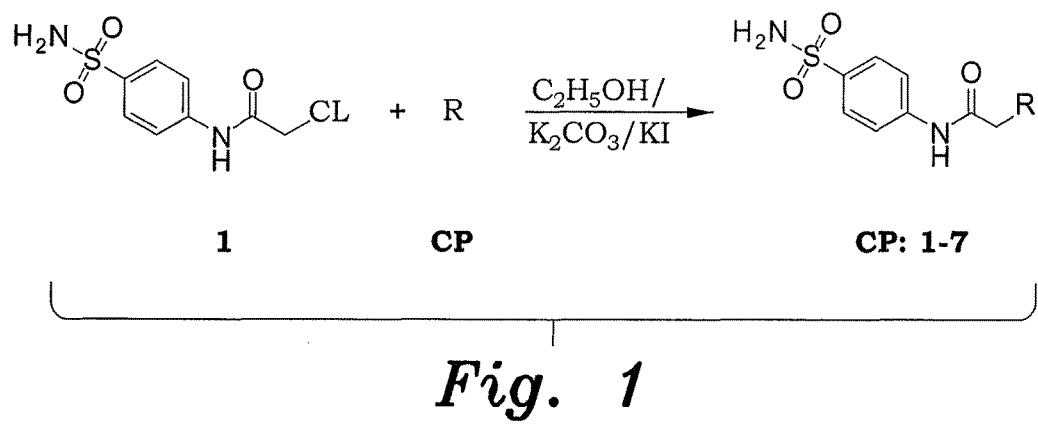
FIG. 1 shows the chemical reaction scheme for preparing the amino substituted acetamide derivatives CP-1-7.

An amino substituted acetamide derivative can include a compound having the following general formula:

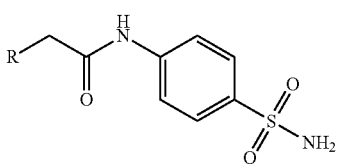

wherein R represents at least one of the following amino substituents,

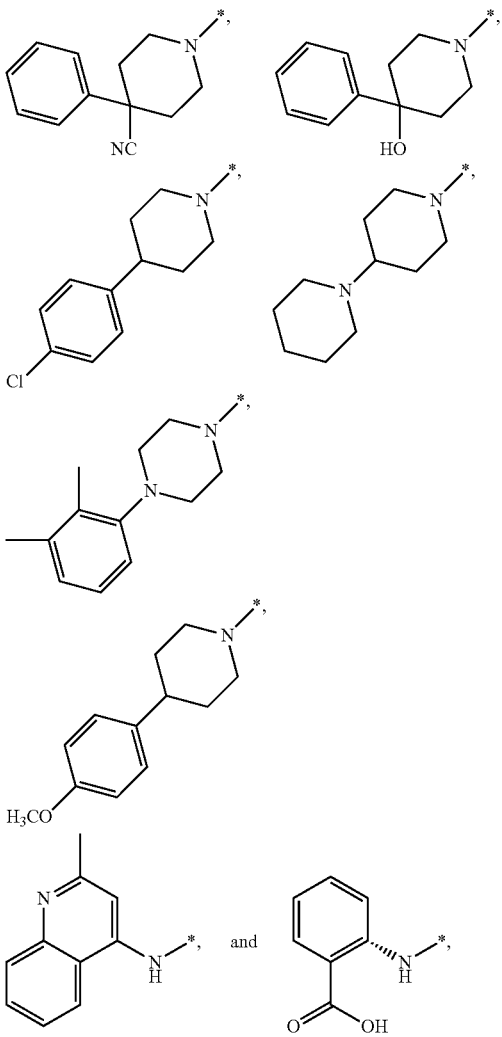

or a pharmaceutically acceptable salt thereof.

The amino substituted acetamide derivative can be useful for treating ulcers and/or ulcerative colitis. For example, the amino substituted acetamide derivative can be an active agent in a pharmaceutical composition for treating ulcerative colitis and/or peptic ulcers. A pharmaceutical composition including the amino substituted acetamide derivative can include one or more pharmaceutically acceptable carriers. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents and the like; for solid oral preparations, suitable carriers and additives include starches, sugars, diluents, granulating agents, lubricants, binders, disintegrating agents and the like. For parenteral use, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. Accordingly, the pharmaceutically acceptable carrier can include alcohol, dimethyl sulfoxide (DMSO), a physiological saline, a lipid based formulation, a liposomal formulation, a nanoparticle formulation, a micellar formulation, a water soluble formulation, a biodegradable polymer, an aqueous preparation, a hydrophobic preparation, a lipid based vehicle, or a polymer formulation.

The amino substituted acetamide derivative or compositions thereof can be administered to a subject by any suitable route for treating ulcers and/or ulcerative colitis. Parenteral, otic, ophthalmic, nasal, inhalable, buccal, sublingual, enteral, topical, oral, peroral, and injectable dosage forms are particularly useful. Particular dosage forms include a solid or liquid dosage forms. Exemplary suitable dosage forms include tablet, capsule, pill, caplet, troche, sache, solution, suspension, dispersion, vial, bag, bottle, injectable liquid, i.v. (intravenous), i.m. (intramuscular) or i.p. (intraperitoneal) administrable liquid and other such dosage forms known to the artisan of ordinary skill in the pharmaceutical sciences.

The amount of the amino substituted acetamide derivative incorporated in a dose can be selected according to the examples provided herein and/or according to known principles of pharmacy. An effective amount or therapeutically effective amount of the amino substituted acetamide derivative is specifically contemplated. By the term "effective amount", it is understood that, with respect to, for example, pharmaceuticals, a pharmaceutically effective amount is contemplated. A pharmaceutically effective amount is the amount or quantity of active ingredient which is enough for the required or desired therapeutic response, or in other words, the amount, which is sufficient to elicit an appreciable biological response when administered to a patient. The appreciable biological response, i.e., anti-ulcerogenic and anti-ulcerative colitis (UC) activities, can occur as a result of administration of single or multiple doses of an active substance. A dose may comprise one or more dosage forms. It will be understood that the specific dose level for any patient will depend upon a variety of factors including the indication being treated, severity of the indication, patient health, age, gender, weight, diet, pharmacological response, the specific dosage form employed, and other such factors. According to an embodiment, about 50 mg/kg to about 100 mg/kg of one or more of the amino substituted acetamide derivatives CP 1-8 can be administered orally to a subject in need thereof for a period of about 15 days.

A method for preparing the amino substituted acetamide derivative can include mixing equimolar concentration of 2-Chloro-N-(4-aminosulphonylphenyl)acetamide with an amine derivative dissolved in ethanol to form a mixture; refluxing the ethanol mixture for a period of time, e.g., about 3 hours to about 5 hours; cooling the mixture and isolating the reaction product by purifying the mixture, e,g., by column chromatography. The amino derivative can include, for example, (4-Cyano-4-phenyl)piperidinyl hydrochloride, (4-Hydroxy-4-phenyl)piperidine, (4-chlorophenyl)piperidine hydrochloride, 4-Piperidinopiperidine, 4-(Methoxyphenyl)piperidine, 1-(2,3-xylyl)piperazine monohydrochloride, 4-Aminoquinaldine, and anthranilic acid.

The present teachings will be understood more readily by reference to the following examples, which are provided by way of illustration.

Example 1

Synthesis of 2-Chloro-N-(4-aminosulphonylphenyl)acetamide (Compound 1)

2-Chloroacetyl chloride (1.12 g, 0.01 mole) was added drop wise with vigorous stirring to a cold suspension of sulfanilamide (1.72 g, 0.01 mole) in 10 ml dichloromethane containing 2 drops triethylamine. Stirring was continued for 1 hour and the separated solid was filtered, washed with ether, dried and crystallized from aqueous-ethanol.

Compound 1

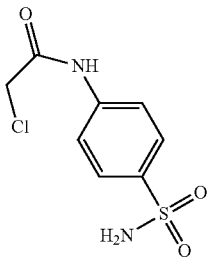

Example 2

Synthesis of 2-(4-Substituted-amino)-N-(4-aminosulphonylphenyl) Acetamide Derivatives (CP1-7)

A mixture of equimolar proportion (0.001 mole) of Compound 1, anhydrous potassium carbonate ($K_2CO_3$), potassium iodide (KI) and the appropriate amine derivative were refluxed in ethanol (20 ml) for 3 hours. The reaction mixture was filtered while hot, cooled and the precipitated solid was cooled and purified by column chromatography to obtain the target compounds CP1-7 in a considerable yield. FIG. 1 shows the chemical reaction scheme for preparing the amino substituted acetamide derivatives CP1-7.

2-[(4-Cyano-4-phenyl)piperidinyl]-N-(4-aminosulphonylphenyl)acetamide (CP-1)

Yield (70%); m.p. 196-198° C.; IR v 3372-3347 (NH, $NH_2$), 1695 (C=O) $cm^{-1}$; $^1H$ NMR (DSMO-$d_6$) δ 2.20 (t, 4H, J=3.2 Hz, $2CH_2$), 2.51 (t, 4H, J=3.7 Hz, $2CH_2$), 3.45 (s, 2H, $CH_2$), 7.05 (s, 2H, $NH_2$), 7.21-7.94 (m, 9H, ArH and $NH_2$), 10.27 (s, $D_2O$ exchangeable, 1H, NH); $^{13}C$ NMR (DSMO-$d_6$) δ 35.3 ($CH_2$), 38.3 ($CH_2$), 50.3 ($CH_2$), 61.2 ($CH_2$), 119.1, 122.1, 125.6, 126.5, 128.0, 128.3, 128.7, 129.0, 138.5, 140.2, 141.4 (Ar—C), 168.9 (C=O); MS m/z (Rel. Int.) 398 (M+, 100). Anal. ($C_{20}H_{22}N_4O_3S$, 398.48) C, 60.28 (60.13); H, 5.56 (5.42); N, 14.06 (13.85); S, 8.05 (8.24).

2-[(4-Hydroxy-4-phenyl)piperidinyl]-N-(4-aminosulphonylphenyl)acetamide (CP-2)

Yield (65%); m.p. 221-223° C.; IR v 3351-3342 (NH, $NH_2$), 1674 (C=O) $cm^{-1}$; $^1H$ NMR (DSMO-$d_6$) δ 2.21 (t, 4H, J=3.2 Hz, $2CH_2$), 2.50 (t, 4H, J=3.7 Hz, $2CH_2$), 3.34 (s, 2H, $CH_2$), 4.87 (s, 1H, OH), 7.29-7.87 (m, 11H, ArH and $NH_2$), 10.17 (s, $D_2O$ exchangeable, 1H, NH); $^{13}C$ NMR (DSMO-d6) δ 39.1 ($CH_2$), 49.3 ($CH_2$), 62.1 ($CH_2$), 69.2 ($CH_2$), 119.1, 124.8, 126.2, 126.5, 127.8, 128.1, 128.4, 128.7, 138.5, 141.5, 150.0 (Ar—C), 169.4 (C=O); MS m/z (Rel. Int.) 389 (M+, 100). Anal. ($C_{19}H_{23}N_3O_4S$, 389.47) C, 58.59 (58.71); H, 5.95 (6.20); N, 10.79 (10.92); S, 8.23 (8.47).

2-[4(4-Chlorophenyl)piperidinyl]-N-(4-aminosulphonylphenyl)acetamide (CP-3)

Yield (63%); m.p. 270-272° C.; IR v 3351-3342 (NH, $NH_2$), 1674 (C=O) $cm^{-1}$; $^1H$ NMR (DSMO-$d_6$) δ 1.64-1.90 (m, 4H, $2CH_2$), 2.22-2.29 (m, 4H, $2CH_2$), 2.71 (m, 1H, CH), 3.35 (s, 2H, $CH_2$), 7.22-7.88 (m, 10H, Ar—H and $NH_2$), 10.09 (s, $D_2O$ exchangeable, 1H, NH); $^{13}C$ NMR (DSMO-d6) δ 37.7 ($CH_2$), 49.2 ($CH_2$), 62.0 ($CH_2$), 69.1 ($CH_2$), 119.1, 126.5, 126.8, 127.7, 130.8, 138.5, 141.5, 149.0 (Ar—C), 169.3 (C=O); MS m/z (Rel. Int.) 409 ($M^+$+2, 26), 407 (M+, 87). Anal. ($C_{19}H_{22}ClN_3O_3S$, 407.91) C, 55.94 (56.11); H, 5.44 (5.27); N, 10.30 (10.16); S, 7.86 (7.70).

2-[4-(1-Piperidino)piperidinyl]-N-(4-aminosulphonylphenyl)acetamide (CP-4)

Yield (62%); m.p. 215-217° C.; IR v 3361-3339 (NH, $NH_2$), 1677 (C=O) $cm^{-1}$; $^1H$ NMR (DSMO-$d_6$) δ 1.45-1.65 (m, 10H, $5CH_2$), 2.21-2.29 (m, 8H, $4CH_2$), 2.72 (m, 1H, CH), 3.35 (s, 2H, $CH_2$), 7.27 (s, 2H, $SO_2NH_2$), 7.66 (d, 2H, J=7.2 Hz, Ar—H),), 7.83 (d, 2H, J=7.5 Hz, Ar—H), 10.09 (s, $D_2O$ exchangeable, 1H, NH); $^{13}C$ NMR (DSMO-d6) δ 24.6, 26.0, 27.4 ($CH_2$), 49.7, 53.1, 61.5, 61.9 ($CH_2$), 118.9, 126.5, 138.5, 141.5 (Ar—C), 169.2 (C=O); MS m/z (Rel. Int.) 380 (M+, 100). Anal. ($C_{18}H_{28}N_4O_3S$, 380.50) C, 56.82 (56.69); H, 7.42 (7.64); N, 14.72 (14.82); S, 8.43 (8.23).

2-[4(4-Methoxyphenyl)piperidinyl]-N-(4-aminosulphonylphenyl)acetamide (CP-5)

Yield (55%); m.p. 175-177° C.; IR v 3354-3340 (NH, $NH_2$), 1675 (C=O) $cm^{-1}$; $^1H$ NMR (DSMO-$d_6$) δ 1.65-1.89 (m, 4H, $2CH_2$), 2.20-2.27 (m, 4H, $2CH_2$), 2.73 (m, 1H, CH), 3.43 (s, 2H, $CH_2$), 6.97 (s, 2H, $SO_2NH_2$), 7.16-7.92 (m, 8H, Ar—H),), 10.38 (s, $D_2O$ exchangeable, 1H, NH); $^{13}C$ NMR (DSMO-d6) δ 20.3, 40.9, 51.6, 53.2, 61.6 ($CH_2$), 118.9, 124.5, 125.7, 126.5, 130.4, 137.2, 141.6, 151.3 (Ar—C), 169.0 (C=O); MS m/z (Rel. Int.) 403 (M+, 100). Anal. ($C_{20}H_{25}N_3O_4S$, 403.50) C, 59.53 (59.33); H, 6.25 (6.47); N, 10.41 (10.63); S, 7.95 (8.13).

2-[4(2,3-Xylyl)piperazinyl]-N-(4-aminosulphonylphenyl)acetamide (CP-6)

Yield (69%); m.p. 241-243° C.; IR v 3368-3347 (NH, $NH_2$), 1671 (C=O) $cm^{-1}$; $^1H$ NMR (DSMO-$d_6$) δ 2.45 (s, 6H, $2CH_3$), 2.57 (t, 4H, J=3.7 Hz, $2CH_2$), 3.41 (s, 2H, $CH_2$), 3.60 (t, 4H, J=3.5 Hz, $2CH_2$), 6.83 (s, 2H, $SO_2NH_2$), 7.27-7.84 (m, 7H, Ar—H),), 10.10 (s, $D_2O$ exchangeable, 1H, NH); $^{13}C$ NMR (DSMO-d6) δ 11.0, 18.3, 49.4, 52.8, 55.1 ($CH_2$), 114.2, 117.3, 118.9, 121.3, 126.5, 135.1, 138.4, 141.5, 145.3, 152.9 (Ar—C), 168.9 (C=O); MS m/z (Rel. Int.) 403 (M+, 71). Anal. ($C_{20}H_{26}N_4O_3S$, 402.51) C, 59.68 (59.62); H, 6.51 (6.75); N, 13.92 (14.16); S, 7.97 (8.16).

2-(2-Methylquinolin-4-ylamino)-N-(4-aminosulphonylphenyl)acetamide (CP-7)

Yield (66%); m.p. >300° C.; IR v 3375-3346 (NH, NH$_2$), 1677 (C=O) cm$^{-1}$; $^1$H NMR (DSMO-d$_6$) δ 2.55 (s, 3H, CH$_3$), 4.01 (s, 2H, CH$_2$), 6.95 (s, 2H, SO$_2$NH$_2$), 7.32-8.01 (m, 9H, Ar—H and NH),), 10.44 (s, D$_2$O exchangeable, 1H, NH) 10.89 (s, D$_2$O exchangeable, 1H, NH); $^{13}$C NMR (DSMO-d6) δ 24.2 (CH$_3$), 52.7 (CH$_2$), 102.0, 117.0, 118.9, 119.2, 122.1, 123.1, 126.6, 128.7, 132.7, 138.8, 141.3, 152.1, 157.8 (Ar—C), 168.2 (C=O); MS m/z (Rel. Int.) 370 (M+, 77). Anal. (C$_{18}$H$_{18}$N$_4$O$_3$S, 370.43) C, 58.36 (58.17); H, 4.90 (5.17); N, 15.12 (15.28); S, 8.66 (8.85).

Table 1 shows the structural formula of the compounds CP1-7 and their formula weights.

TABLE 1

| Code | Chemical Structure | Mol. Wt. |
| --- | --- | --- |
| CP-1 | 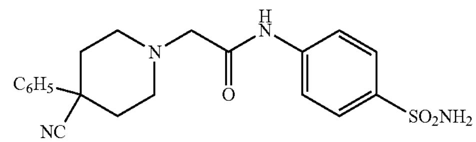 | 398.48 |
| CP-2 | 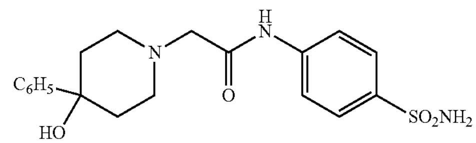 | 389.14 |
| CP-3 | 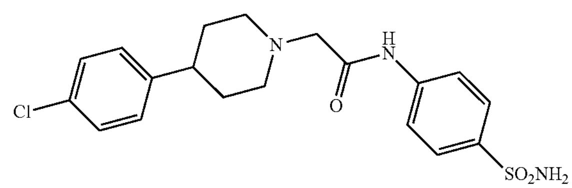 [SMILES: NS(=O)(=O)c1ccc(NC(=O)CN2CCC(c3ccc(Cl)cc3)CC2)cc1] | 407.91 |
| CP-4 | 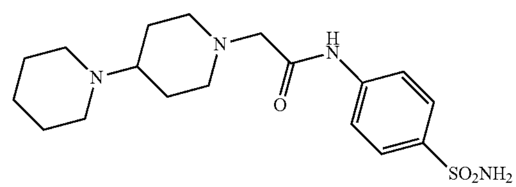 [SMILES: NS(=O)(=O)c1ccc(NC(=O)CN2CCC(N3CCCCC3)CC2)cc1] | 380.19 |
| CP-5 | 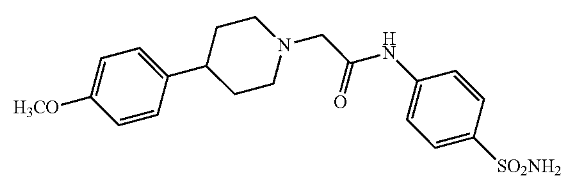 [SMILES: COc1ccc(C2CCN(CC(=O)Nc3ccc(S(N)(=O)=O)cc3)CC2)cc1] | 403.51 |
| CP-6 | 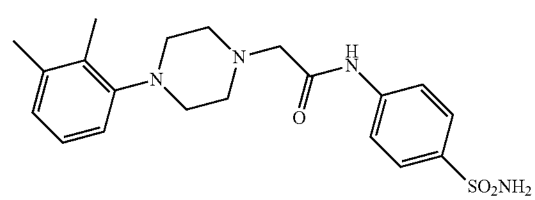 [SMILES: Cc1cccc(N2CCN(CC(=O)Nc3ccc(S(N)(=O)=O)cc3)CC2)c1C] | 402.51 |
| CP-7 | 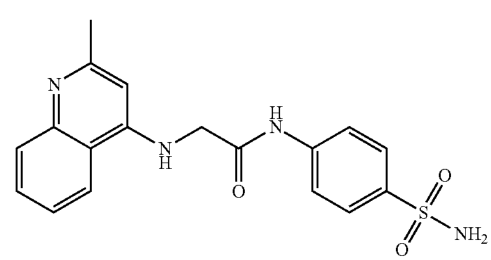 [SMILES: Cc1cc(NCC(=O)Nc2ccc(S(N)(=O)=O)cc2)c2ccccc2n1] | 370.43 |

Example 3

Synthesis of 2-(2-Hydroxycarbonylphenylamino)-N-(4-aminosulphonylphenyl)acetamide (CP8)

Figure 2:
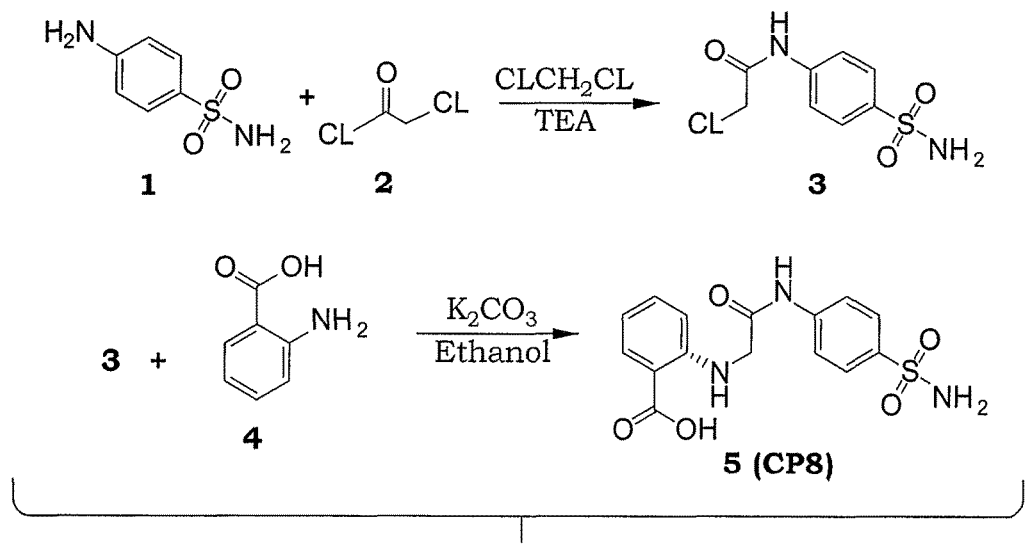
FIG. 2 shows the chemical reaction scheme for preparing the 2-hydroxycarbonylphenylamino amino acetamide derivative, compound 5 (CP8).
Figure 3A:
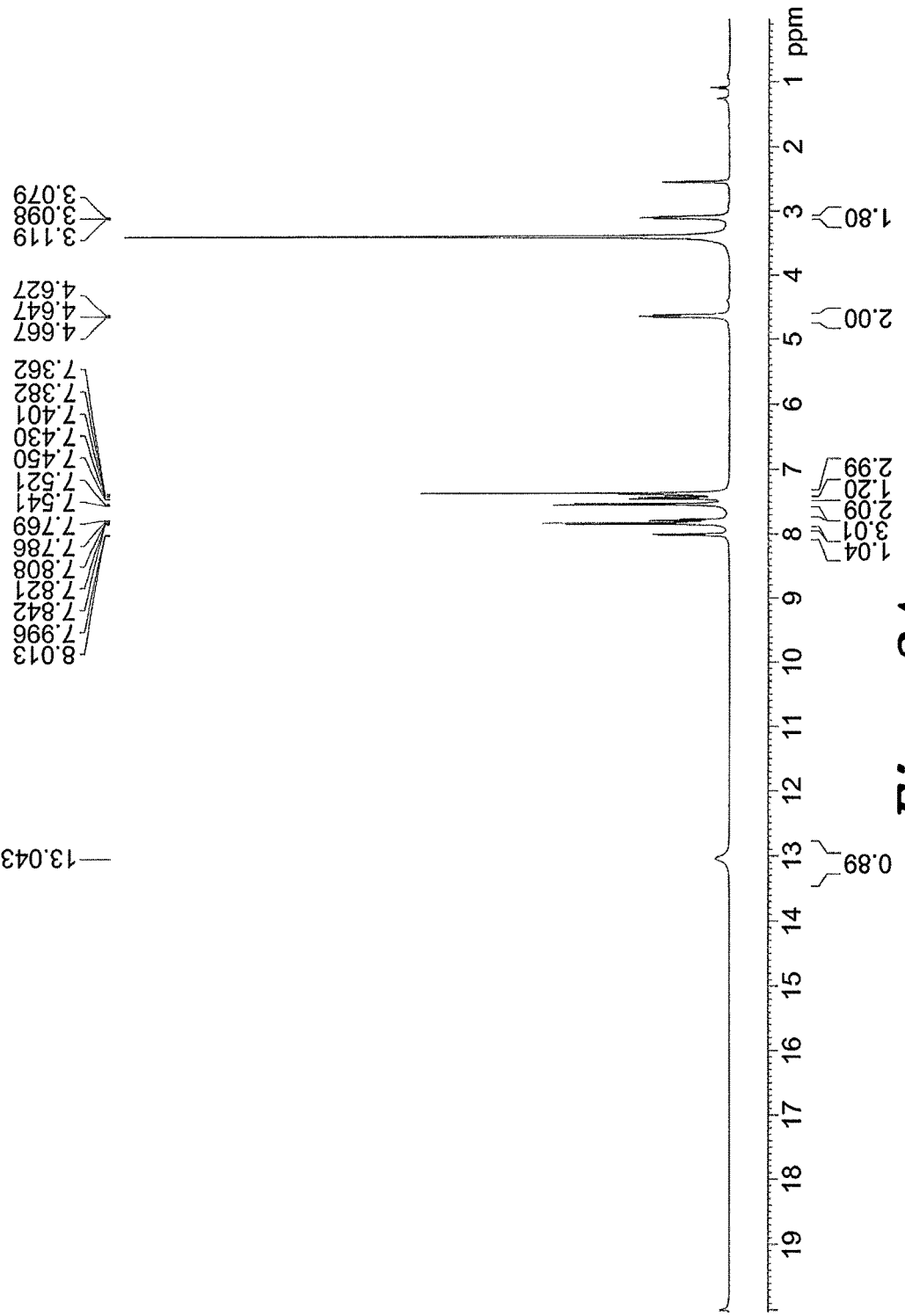
FIG. 3A shows the $^1$H-NMR of the compound 2-(2-Hydroxycarbonylphenylamino)-N-(4-aminosulphonylphenyl)acetamide (CP-8).
Figure 3B:
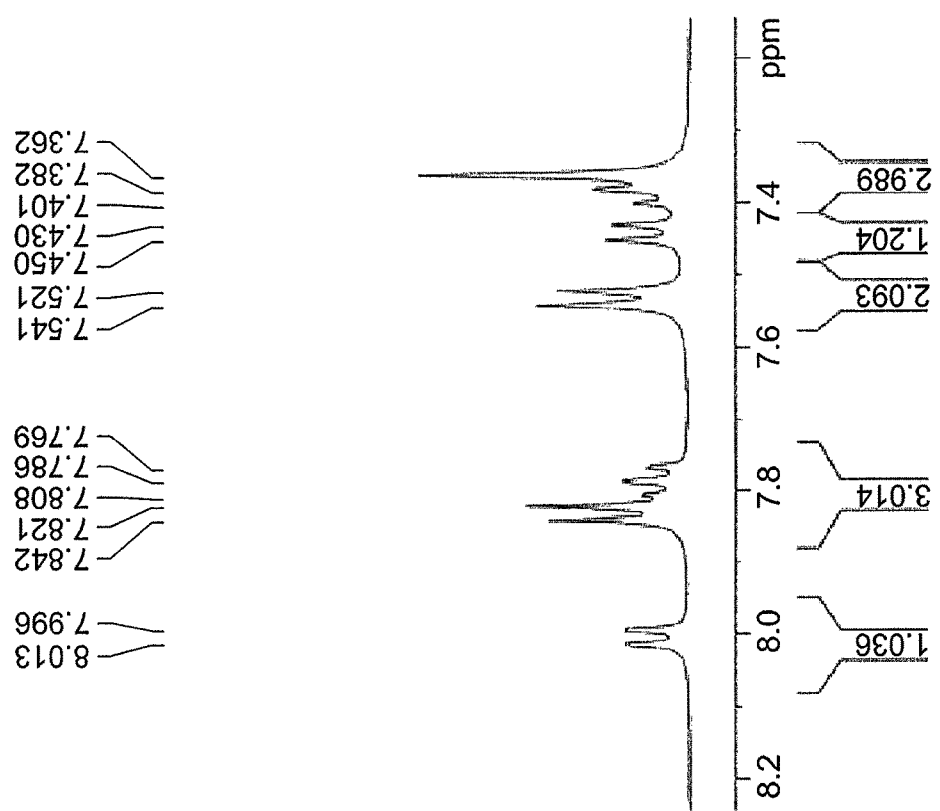
FIG. 3B shows the $^1$H-NMR of the compound 2-(2-Hydroxycarbonylphenylamino)-N-(4-aminosulphonylphenyl)acetamide (CP-8) from 8.2 to 7.0 PPM.
Figure 4:
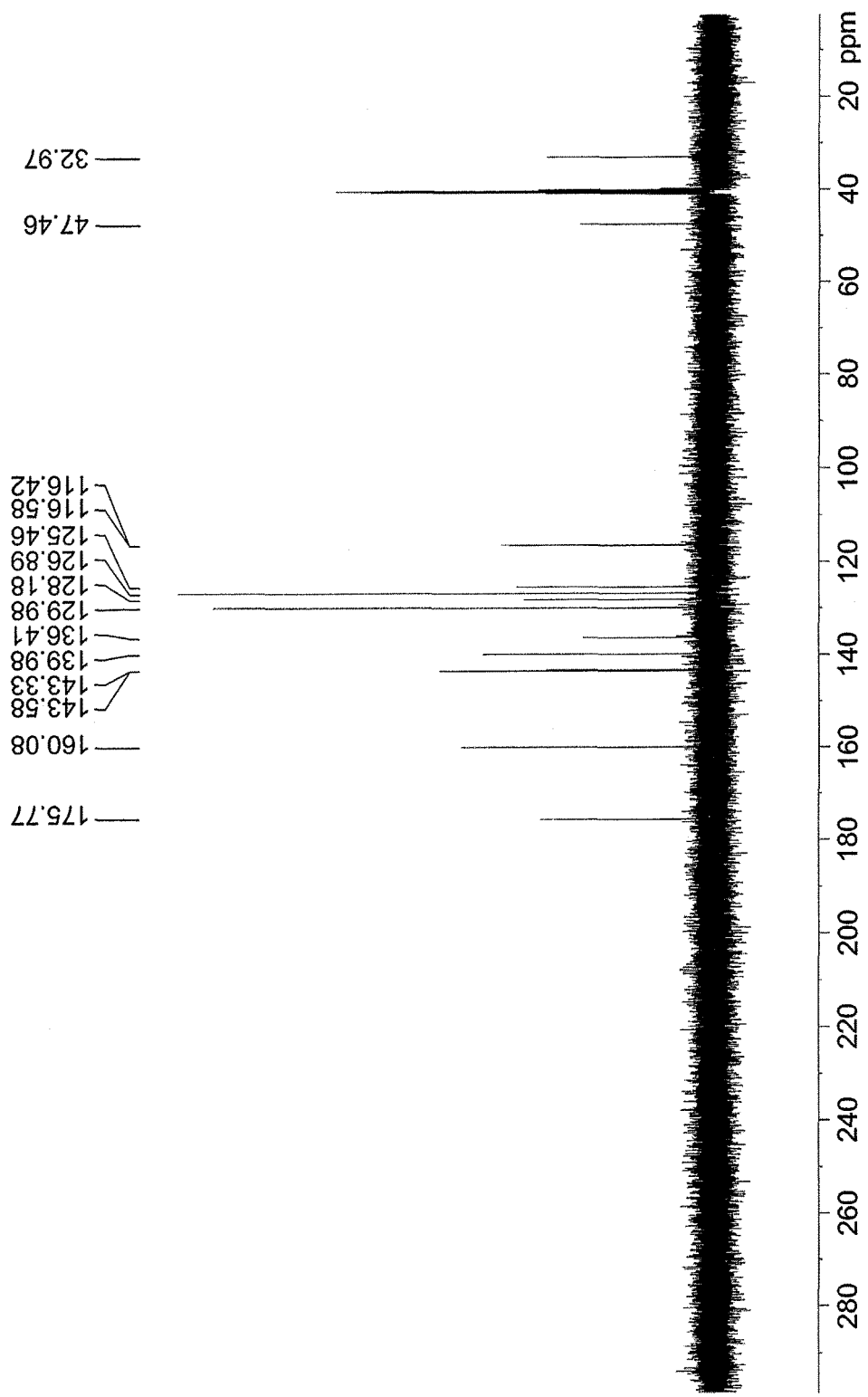
FIG. 4 shows the $^{13}$C-NMR of the compound 2-(2-Hydroxycarbonylphenylamino)-N-(4-aminosulphonylphenyl)acetamide (CP-8).

FIG. 2 shows the chemical reaction scheme for preparing the acetamide derivative compound 5 (CP8). An equimolar proportion of both 2-chloro-N-(4-aminosulphonylphenyl) acetamide (0.248 g, 0.001 mole) (compound 1) and anthranilic acid was boiled in ethanol containing catalytic amount of triethylamine in the presence of potassium iodide (0.32 g) for 5 hours. On cooling, the separated solid filtered, washed with water, dried and crystallized from ethanol to afford 2-(2-Hydroxycarbonylphenylamino)-N-(4-aminosulphonylphenyl)acetamide CP 8: Yield, 52%; m.p. ° C.; $^1$H NMR (DMSOd$_6$): 2.52 (s, 1H, NH, D$_2$O exchange.), 3.26 (s, 2H, CH$_2$), 4.21 (s, 2H, NH$_2$, D$_2$O exchange.), 7.30 (s, 1H, NH, D$_2$O exchange.), 7.67-7.92 (m, 8H, Ar—H), 10.55 (s, 1H, OH, D$_2$O exchange). $^{13}$C NMR: δ 54.2 (CH$_2$), 108.1, 114.5, 118.3, 122.7, 126.7, 132.1, 133.8, 136.4, 141.4, 150.6 (Ar—C), 167.6, 169.0 (2C=O). MS (EI): m/z [M$^+$, %]. Anal. (C$_{15}$H$_{15}$N$_3$O$_5$S) C, H, N.

The biological activities of the investigational compounds (CP1-8) were investigated as follows. Swiss albino mice of both sexes (26-30 g) and male Wistar rats (180-200 g) were purchased from the animal house of King Saud University, KSA. Animals were housed in standard polypropylene cages with wire mesh top and maintained under standard conditions (temperature 23±1.0° C., humidity 55±10%, 12 h light/12 h dark cycle). They were fed a standard pellet diet with water ad libitum and were allowed to adapt to the laboratory environment for one week before experimentation.

The oral median lethal dose (LD50) of the target compound was determined as described by Lorke (1983). Swiss albino mice in groups of six, received one of 50, 100, 500, or 1000 mg/kg doses of the target compound. Control animals were received the vehicle and kept under the same conditions. Signs of acute toxicity and number of deaths per dose within 24 h were recorded.

Evaluation of the anti-ulcerogenic activity was carried out using absolute ethanol-induced ulcer model as described by Bighettia et al. (2005). Eighteen male Wistar rats were divided into 3 groups each of 6 rats. Group 1 received the vehicle and served as control ulcer, Group 2 received ranitidine (100 mg/kg) and served as standard, and Groups 3 received the target compound at a dose of 50 mg/kg for CP1-7 and a dose of 100 mg/kg for CP8.

Rats of all groups were fasted for 24 h then all medications were administered orally. One hour after treatment, the animals received an oral dose of absolute ethanol (1 ml/200 g) and then sacrificed one hour later, by ether inhalation, the stomachs were rapidly removed, opened along their greater curvature and gently rinsed under running tap water.

Number of lesions in the glandular part of the stomach were measured under an illuminated magnifying microscope (10×). Long lesions were counted and their lengths were measured. Petechial lesions were counted, and then each five petechial lesions were taken as 1 mm of ulcer.

The lesion scores in the mucosal lesions were quantified by the scoring system (0-5) 0=no damage, 1=Local edema and inflammation without ulcers; 2=One ulcer without inflammation; 3=one to two ulcers with inflammation & lesion diameter <1 cm; 4=More than two ulcers with lesion diameter 1-2 cm; 5=Sever ulceration with lesion diameter >2 cm (Morris et al., 1989).

In order to calculate the Ulcer Index (mm), the sum of the total length of long ulcers and petechial lesions in each group of rats was divided by its number. The curative ratio was determined according to the formula:

$$\% \text{ Protection of Control Ulcer} = \frac{[\text{Control } UI - \text{Test } UI]}{\text{Control } UI} \times 100$$

Example 4

Measurement of Anti-Ulcerative Colitis Activity

Groups of animals each of 6 rats were used for assessing the anti-ulcerative colitis activity. The first group received dexamesathone at dose 0.1 mg/kg orally to serve as standard; two other groups received water orally and served as normal control and control colitis. Other groups received the tested compounds CP 1-7 at a dose 50 mg/kg and tested compound CP 8 at a dose of 100 mg/kg. Ulcerative colitis was induced by slowly infusion of 2 mL (4%, v/v) acetic acid in saline into the colon through the catheter. Two hours after the induction of colitis, animals received the 1st dose of all medication, then all groups received medication for 5 consecutive days, two hours after the last dose, animals were sacrificed by ether anesthesia, colonic segments (8 cm in length and 3 cm proximal to the anus) were excised, opened and were used for macroscopic scoring (Awaad et al., 2013).

The colonic lesions were assessed as follows. The colon specimens were weighted and wet weight/length ratio was calculated for all the rats. The specimens were examined under a dissecting microscope and the mucosal lesions were quantified by the scoring system (0-5) given by Awaad et al., (2013) after some modifications. The lesion scores were determined as follows: 0=no damage, 1=Local edema and inflammation without ulcers; 2=One ulcer without inflammation; 3=one to two ulcers with inflammation & lesion diameter <1 cm; 4=More than two ulcers with lesion diameter 1-2 cm; 5=Sever ulceration with lesion diameter >2 cm.

The ulcer area was measured using plane glass square. Each cell on the glass square was 1 mm$^2$ in area and the number of cells was counted and the ulcer area was determined for each colon. The ulcer index was measured by summing the lesion score and the ulcer area for each colon specimen (Awaad et al, 2013).

The effect on liver and kidney functions using the derivatives were investigated as follows. Male Wister rats were divided into 2 groups, each of 10 rats. The 1$^{st}$ group was left as a control and administered the vehicle orally, while the other group was orally administered the synthesized compounds in a dose of 50 mg/kg (for CP 1-7) or a dose of about 100 mg/kg (for CP 8). After the examination period, 6 h after the last dose blood samples were collected from the orbital plexus of rats. Samples were left to clot at room temperature for 30 min then centrifuged at 1000 rpm for 20 min.

The collected sera were used for determination of the activity of both (AST) aspirate aminotransferase and (ALT) alanine aminotransferase as liver markers. In addition, levels of blood urea, serum creatinine were also estimated as kidney markers (Awaad et al., 2013).

All values were expressed as mean±S.D. (standard deviation). Statistical analysis was done by using SPSS 10. Statistical significance of differences between two means was assessed by unpaired Student's 't' test. Differences at p<0.05, 0.01, and 0.001 were considered statistically significant.

The target compounds were obtained from the key starting material 2-chloro-N-(4-aminosulphonylphenyl)-acetamide, 1, with the appropriate amine derivative by nucleophylic displacement reaction. The reaction was activated by using potassium carbonate as acid acceptor in presence of potassium iodide to make it easier to release the chlorine atom. The structure of the target compounds was confirmed by IR, NMR and mass spectra. Generally, the obtained data are in accordance with the proposed structures. IR spectra showed the presence of NH and $NH_2$ at around 3350 $cm^{-1}$, and the carbonyl group at around 1670 $cm^{-1}$. The $^1H$ NMR spectra showed the presence of NH and $SO_2NH_2$ in addition to methylene and carbonyl in the $^{13}C$ spectra. The mass spectra showed the molecular ion peak with relative intensity ranging from 100-77%.

Determination of median Lethal Dose ($LD_{50}$). The target compounds in doses up to 1000 mg/kg did not produce any behavioral changes and mortality in mice. Therefore, it can be categorized as highly safe since substances possessing $LD_{50}$ higher than 50 mg/kg are nontoxic (Soliman et al., 2012).

The present results showed that the target compounds possessed a potent anti-ulcerogenic activity with different potentials. The most effective compound was CP-4, which produced percent protection of control ulcer 97.7% followed by CP-3, which produced 90.3% protection, while the standard drug ranitidine (100 mg/kg) produced 49.2% as presented in Table 2. The tested compound CP-1 showed the lowest activity amount among the target compounds since it produced only 55.5% protection. Overall, the target compounds were significantly more effective than the standard drug in reducing the ulcer index.

Table 2 shows the curative anti-ulcerogenic effect of target compounds CP-1-7 on absolute alcohol-induced ulcer in rats.

TABLE 2

| Gp | Dose mg/kg | score | no of ulcers | ulcer index | % protection |
|---|---|---|---|---|---|
| Control | | 4.00 | 13.20 ± 1.30 | 95.20 ± 1.10 | 0 |
| Ranitidine | 100 | 2.20 | 8.60* ± 3.05 | 48.40* ± 1.24 | 49.2 |
| CP-1 | 50 | 3.20 | 7.20* ± 0.84 | 42.40* ± 1.14 | 55.5 |
| CP-2 | 50 | 3.20 | 7.60* ± 1.14 | 26.80*@ ± 1.64 | 71.9 |
| CP-3 | 50 | 2.20 | 2.80*@ ± 0.84 | 8.80 ± 41.30 | 90.8 |
| CP-4 | 50 | 2.00 | 1.40*@ ± 0.55 | 2.20*@ ± 0.84 | 97.7 |
| CP-5 | 50 | 2.40 | 3.40*@ ± 0.89 | 15.60*@ ± 1.14 | 83.6 |
| CP-6 | 50 | 3.00 | 6.80* ± 0.84 | 11.00*@ ± 0.71 | 88.5 |
| CP-7 | 50 | 3.60 | 8.00* ± 0.71 | 34.20*@ ± 1.10 | 64.1 |

Data are expressed as mean ± SD, n = 6,
*Significantly different from control ulcer at p < 0.05.
@Significantly different from ranitidine at p < 0.05.

Table 3 shows the anti-ulcerogenic effect of target CP 8 on absolute alcohol-induced ulcer in rats of the compound.

TABLE 3

| Groups | Dose mg/kg | score | no of ulcers | ulcer index | % protection |
|---|---|---|---|---|---|
| Control ulcer | — | 3.40 | 9.20 ± 0.84 | 17.00 ± 0.71 | 0 |
| Ranitidine | 100 | 2.20 | 7.20* ± 0.84 | 7.00* ± 1.00 | 58.8 |
| Target compound | 100 | 1.20 | 3.00*@ ± 0.71 | 2.2*@ ± 0.76 | 87.1 |

Data are expressed as mean ± SD, n = 6,
*Significantly different from control ulcer at p < 0.01.
@Significantly different from ranitidine at p < 0.01

Similarly, the results presented in Table 3 showed that the target compound CP8 possessed a potent anti-ulcerogenic activity. It produced percent protection of control ulcer 87.1% at dose 100 mg/kg, while the standard drug ranitidine (100 mg/kg) produced 58.8% (Table 3). The target compound was significantly more effective than the standard in reducing ulcer index and ulcer score.

Table 4 displays the effect of target compounds on acetic acid induced colitis in rats.

TABLE 4

| GP | Score | Ulcer area (mm$^2$) | Ulcer index | Wt/l | % Protection |
|---|---|---|---|---|---|
| Normal control | 0 | 0 | 0 | 0.38 ± 0.05 | 0 |
| Control colitis | 4.00 ± 0.89 | 40.20 ± 0.75 | 44.20 ± 1.33 | 0.95 ± 0.07 | 0 |
| Dexamethasone | 2.00* ± 0.63 | 16.00* ± 0.63 | 18.00* ± 1.10 | 0.52 ± 0.07 | 59.3 |
| CP-1 | 2.67* ± 0.52 | 27.50*@ ± 1.38 | 30.17*@ ± 1.60 | 0.79 ± 0.08 | 31.7 |
| CP-2 | 2.33* ± 0.52 | 20.17*@ ± 1.17 | 22.50*@ ± 1.05 | 0.74 ± 0.02 | 49.1 |
| CP-3 | 1.67*@ ± 0.52 | 14.17*@ ± 0.98 | 15.83*@ ± 1.17 | 0.64 ± 0.05 | 64.2 |
| CP-4 | 3.00 ± 0.63 | 30.00*@ ± 1.41 | 33.00*@ ± 1.67 | 0.84 ± 0.02 | 25.3 |
| CP-5 | 2.67* ± 0.52 | 31.67*@ ± 1.37 | 34.33*@ ± 1.63 | 0.75 ± 0.02 | 22.3 |
| CP-6 | 2.67* ± 0.52 | 28.00*@ ± 1.41 | 30.67*@ ± 1.21 | 0.71 ± 0.05 | 30.6 |
| CP-7 | 1.50*@ ± 0.55 | 13.17*@ ± 1.17 | 14.67*@ ± 0.82 | 0.49 ± 0.02 | 66.8 |

*Significantly different from control colitis at p < 0.05.
@Significantly different from Dexamethasone at p < 0.05.

Table 5 shows the effect of target compounds on acetic acid induced-colitis in rats using the compound CP8.

TABLE 5

| Groups | Lesion score (0-5) | Ulcer area (mm²) | Wet W/L (g/8 cm) | % Protection of control colitis |
|---|---|---|---|---|
| Normal control | 0.0 ± 0.0 | 0.0 ± 0.0 | 0.38 ± 0.05 | — |
| Control colitis | 4.00 ± 0.89 | 40.20 ± 1.21 | 0.95 ± 0.07 | — |
| Dexamethasone (0.1 mg/kg) | 1.67* ± 0.75 | 16.00* ± 0.63 | 0.52* ± 0.07 | 60 |
| Target compound (100 mg/kg) | 1.83* ± 0.41 | 15.83* ± 0.98 | 0.51* ± 0.03 | 64.2 |

*Significantly different from control colitis at $p < 0.01$.

The model of acetic acid induced colitis shares many of the histologic features of ulcerative colitis in human beings including mucosal edema and sub-mucosal ulceration. As depicted in the Tables, no abnormal changes were observed in rats of the control group, which suggests that the handling procedure had no interference with the experimental outputs. Macroscopic damage parameters of the colon of control colitis rats after rectal infusion of acetic acid revealed dark brown lesions, mucosal hyperemia, edema, erosion, and ulceration. The inflammatory changes of the intestinal tract were associated with a significant increase of wet weight/length of the colon specimens as an indicator of inflammation.

The curative effect of the tested compounds CP1-7 at dose 50 mg/kg on acetic acid-induced colitis in rats is shown in Table 4. The tested compounds administrated orally to rats showed a potent anti-ulcerative colitis activity with different potentials. They induced a significant decrease in ulcer score, ulcer area, ulcer index and weight/length of the colon specimens. The percent protection of control colitis ranged from 66.8% for CP-7 to 22.3% for CP-5; however, the percent protection for dexamesathone (0.1 mg/kg) was 59.3%. The effect of the tested compounds CP-7 and CP-3 at dose 50 mg/kg were significantly more effective than dexamesathone (0.1 mg/kg) in reducing all parameters.

Similarly, the percent protection of control colitis was 64.2% for the target compound CP8; however the percent protection for dexamesathone (0.1 mg/kg) was 60% as shown in Table 5.

The effect on liver and kidney functions were assessed. It was found that the liver functions were not affected as there is no effect on the activity of both aspartate aminotransferase (AST) and alanine aminotransferase (ALT) in animals received the tested compounds (Tables 6 and 7), so the compounds didn't reveal hepatotoxic manifestation. These results on kidney functions showed that only CP1 can slightly elevate blood urea concentration, and both compounds CP-3 and CP-4 slightly elevated serum creatinine. In addition, no apparent nephrotoxic manifestations were recorded.

Table 6 shows the effect of amino acid-sulfanilamide compound on liver and kidney functions of rats using compounds CP-1-7.

TABLE 6

| GP | ALT(U/l) | AST(U/l) | Blood Urea (mg/dl) | Serum Creatinine (mg/dl) |
|---|---|---|---|---|
| Normal control | 37.25 ± 0.26 | 47.31 ± 0.51 | 53.67 ± 0.84 | 0.89 ± 0.02 |
| CP-1 | 35.77 ± 1.60 | 44.43 ± 1.57 | 70.51* ± 0.89 | 0.88 ± 0.03 |
| CP-2 | 39.70 ± 0.22 | 66.28 ± 0.40 | 52.55 ± 1.24 | 0.86 ± 0.03 |
| CP-3 | 36.87 ± 1.28 | 44.16 ± 1.57 | 46.02 ± 1.10 | 01.01* ± 0.09 |
| CP-4 | 36.87 ± 1.28 | 44.16 ± 1.57 | 47.96 ± 0.84 | 0.94* ± 0.07 |
| CP-5 | 36.35 ± 1.26 | 44.09 ± 1.25 | 55.92 ± 0.55 | 0.86 ± 0.07 |
| CP-6 | 36.02 ± 1.58 | 44.7 ± 1.66 | 51.00 ± 0.89 | 0.83 ± 0.08 |
| CP-7 | 36.33 ± 1.35 | 46.16 ± 1.48 | 53.00 ± 0.14 | 0.85 ± 0.09 |

Data are expressed as mean ± SD, n = 10

It is evident that the liver functions were not affected as there is no effect on the activity of both AST and ALT in animals received the tested compounds (Table 6), so the compounds didn't reveal hepatotoxic manifestation. These results on kidney functions showed that, only CP1 can slightly elevate blood urea concentration, and both compounds CP-3 and CP-4 slightly elevated serum creatinine. In addition, no apparent nephrotoxic manifestations were recorded. Table 7 shows the effect of amino acid-sulfanilamide compound on liver and kidney functions of rats using compound CP8.

TABLE 7

| Groups | ALT(U/l) | AST(U/l) | Blood Urea (mg/dl) | Creatinine (mg/dl) |
|---|---|---|---|---|
| Control | 41.25 ± 0.35 | 65.31 ± 0.51 | 71.44 ± 1.36 | 0.88 ± 0.02 |
| Compound C (100 mg/kg) | 39.70 ± 0.22 | 66.28 ± 0.40 | 68.60 ± 1.9 | 0.86 ± 0.03 |

Data are expressed as mean ± SD, n = 10.

Both liver and kidney functions were not affected using compound 5 (CP8) as there is no significant difference between control and test group in all experiments, at the 0.05 level of probability as shown in Table 7. These results showed that, the compound 5 (CP8) didn't reveal hepatotoxic manifestation. In addition, no apparent nephrotoxic manifestations were recorded. It was found that the activity of the investigated compounds differed according to the structure of the compound and that there was a structure-activity relationship (SAR) between the tested compounds.

It is to be understood that the present invention is not limited to the embodiments described above, but encompasses any and all embodiments within the scope of the following claims.

We claim:

1. An amino substituted acetamide derivative, comprising the structural formula:

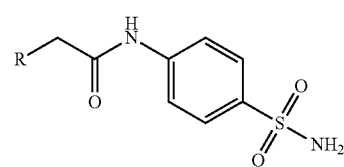

wherein R is a compound selected from the group consisting of

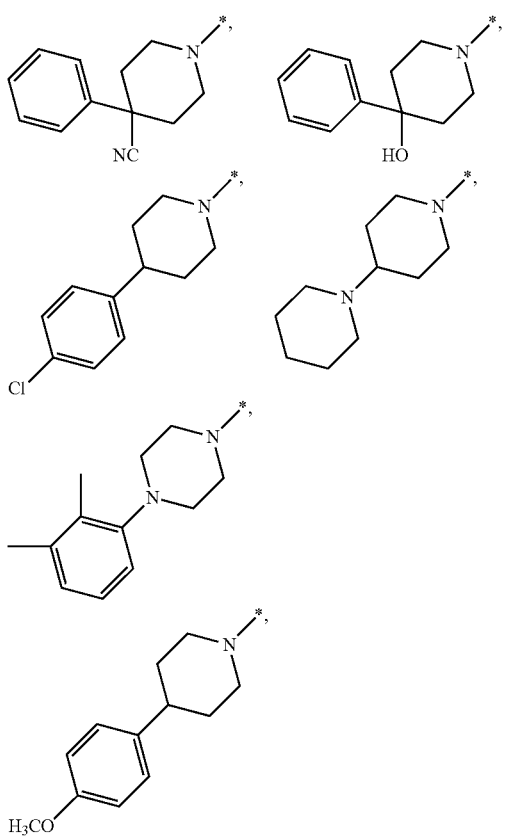

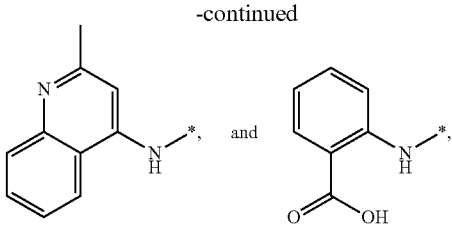

or a pharmaceutically acceptable salt thereof.

2. A pharmaceutical composition comprising the amino substituted acetamide derivative according to claim 1 and a pharmaceutically acceptable carrier.

3. A method for preparing the amino substituted acetamide derivative of claim 1, comprising:
 mixing an equimolar concentration of 2-Chloro-N-(4-aminosulphonylphenyl)acetamide with an amine derivative dissolved in ethanol to form a mixture;
 refluxing the mixture;
 cooling the mixture; and
 isolating the amino substituted acetamide derivative from the mixture.

4. The method of claim 3, wherein the amine derivative is selected from the group consisting of (4-Cyano-4-phenyl)piperidinyl hydrochloride, (4-Hydroxy-4-phenyl)piperidine, (4-chlorophenyl)piperidine hydrochloride, 4-Piperidinopiperidine, 4-(Methoxyphenyl)piperidine, 1-(2,3-xylyl)piperazine monohydrochloride, 4-Aminoquinaldine and anthranilic acid.

* * * * *